US010851040B2

United States Patent
Kawamura et al.

(10) Patent No.: US 10,851,040 B2
(45) Date of Patent: Dec. 1, 2020

(54) RESTARTING METHOD

(71) Applicant: NIPPON KAYAKU KABUSHIKI KAISHA, Tokyo (JP)

(72) Inventors: Tomoyuki Kawamura, Yamaguchi (JP); Tomoaki Kobayashi, Tokyo (JP); Tatsuhiko Kurakami, Yamaguchi (JP); Hideo Yoshida, Yamaguchi (JP)

(73) Assignee: NIPPON KAYAKU KABUSHIKI KAISHA, Tokyo (JP)

( * ) Notice: Subject to any disclaimer, the term of this patent is extended or adjusted under 35 U.S.C. 154(b) by 51 days.

(21) Appl. No.: 16/088,690

(22) PCT Filed: Mar. 29, 2017

(86) PCT No.: PCT/JP2017/012969
§ 371 (c)(1),
(2) Date: Sep. 26, 2018

(87) PCT Pub. No.: WO2017/170721
PCT Pub. Date: Oct. 5, 2017

(65) Prior Publication Data
US 2020/0048175 A1    Feb. 13, 2020

(30) Foreign Application Priority Data

Mar. 29, 2016  (JP) ................. 2016-066023

(51) Int. Cl.
*C07C 45/35* (2006.01)
*B01J 23/887* (2006.01)
*B01J 38/02* (2006.01)
*C07C 51/235* (2006.01)
*C07C 47/22* (2006.01)
*C07C 57/04* (2006.01)

(52) U.S. Cl.
CPC ........... *C07C 45/35* (2013.01); *B01J 23/8876* (2013.01); *B01J 38/02* (2013.01); *C07C 51/235* (2013.01); *C07C 47/22* (2013.01); *C07C 57/04* (2013.01)

(58) Field of Classification Search
CPC ....... C07C 45/35; C07C 47/22; C07C 51/235; C07C 57/04; B01J 23/8876; B01J 38/02
USPC ........................................................ 562/534
See application file for complete search history.

(56) References Cited

U.S. PATENT DOCUMENTS

| | | | |
|---|---|---|---|
| 8,415,498 B2 | 4/2013 | Tanimoto et al. | |
| 9,440,904 B2 | 9/2016 | Nakazawa et al. | |
| 9,580,376 B2 | 2/2017 | Kawamura et al. | |
| 2011/0015432 A1 | 1/2011 | Tanimoto et al. | |
| 2012/0095267 A1 | 4/2012 | Macht et al. | |
| 2016/0145180 A1 | 5/2016 | Kawamura et al. | |
| 2016/0145181 A1 | 5/2016 | Nakazawa et al. | |

FOREIGN PATENT DOCUMENTS

| | | | |
|---|---|---|---|
| JP | 2009-263352 | 11/2009 | |
| JP | 2009263352 A * | 11/2009 | |
| JP | 2011/183313 | 9/2011 | |
| JP | 2014-500855 | 1/2014 | |
| WO | WO2009/125658 | 10/2009 | |
| WO | WO-2009125658 A1 * | 10/2009 | ............. C07C 47/22 |
| WO | WO2015/008814 | 1/2015 | |
| WO | WO2015/008815 | 1/2015 | |
| WO | WO-2015008814 A1 * | 1/2015 | ........... C07C 51/252 |
| WO | WO-2015008815 A1 * | 1/2015 | ........... C07C 51/252 |

OTHER PUBLICATIONS

Japanese Office Action in counterpart Application No. 2016-066023, dated Sep. 6, 2019 (along with English-language translation thereof).
International Search Report in International Bureau of WIPO Patent Application No. PCT/JP2017/012969, dated Jul. 4, 2017.
Submission of Publications in related Japanese application No. JP2016-66023, dated Jan. 30, 2019 (and English-translation thereof).
Submission of Publications in related Japanese application No. JP2016-66023, dated Nov. 28, 2019 (and English-translation thereof).
European Extended Search Report in counterpart European Application No. 17775255.7, dated Oct. 15, 2019.
Official Communication issued in Indian Patent Office Patent Application No. 201837030753, dated Mar. 9, 2020.
Official Communication issued in Japanese Patent Office Patent Application No. 2016-066023, dated Mar. 30, 2020 and English Translation Thereof.

* cited by examiner

*Primary Examiner* — Deborah D Carr
(74) *Attorney, Agent, or Firm* — Greenblum & Bernstein, P.L.C.

(57) ABSTRACT

A method for producing at least one oxidation product selected from the group consisting of acrolein and acrylic acid is provided. This method can alleviate concerns about deterioration of a gas-phase oxidation catalyst and reaction runaway in a restart period after a shutdown, and can allow the reaction to proceed in a stable state. Using a fixed-bed reactor filled with a gas-phase oxidation catalyst, at least one source gas selected from the group consisting of propylene and acrolein is subjected to a gas-phase contact oxidation reaction while a heating medium is caused to contact with or circulate through the fixed-bed reactor and thereby to heat the fixed-bed reactor. The temperature of the heating medium when the load is maximum in the restart period after the shutdown is controlled to be lower than the temperature of the heating medium when the load is maximum in an initial start-up period.

8 Claims, No Drawings

RESTARTING METHOD

TECHNICAL FIELD

The present invention relates to a method for producing at least one oxidation product selected from the group consisting of acrolein and acrylic acid.

BACKGROUND ART

Conventional methods for obtaining an oxidation product include a method for producing acrylic acid by a two-step gas-phase contact oxidation reaction of propylene with use of a fixed-bed reactor filled with a gas-phase oxidation catalyst and heated by a heating medium (a reaction bath), and a method for producing methacrylic acid by a two-step gas-phase contact oxidation reaction of isobutylene with use of a fixed-bed reactor filled with a gas-phase oxidation catalyst.

Such gas-phase contact oxidation reactions each using a fixed-bed reactor are normally performed continuously, but can be temporarily shut down (stopped) for troubleshooting in a start-up period or a stable operation (a steady operation), for maintenance of the fixed-bed reactor, for air treatment of the gas-phase oxidation catalyst, or for other reasons. After the shutdown, the gas-phase contact oxidation reaction is restarted (started again). In this regard, the inventors of the present application have made an investigation and found that the temperature condition in the initial start-up period is not preferable in the restart period after the shutdown. In other words, the inventors of the present application have found a fact that the catalyst is more active in the restart period after the shutdown than in the initial startup period, and have found a problem that, if the temperature of the heating medium at the restart is the same as the initial start-up temperature, the maximum temperature (the hot spot temperature) in the catalyst layer gets higher than a desired temperature range, causing an unstable state with concerns about deterioration of the gas-phase oxidation catalyst and reaction runaway.

PTL 1 teaches a method for producing at least one reaction product selected from the group consisting of unsaturated aliphatic aldehydes having 3 to 4 carbon atoms, unsaturated hydrocarbons, and unsaturated fatty acids having 3 to 4 carbon atoms, with use of a fixed-bed reactor containing a catalyst. At least one reaction source gas selected from the group consisting of hydrocarbons having 3 to 4 carbon atoms and tertiary butanol or at least one reaction source gas selected from the group consisting of unsaturated aliphatic aldehydes having 3 to 4 carbon atoms is subjected to gas-phase contact oxidation. In this method, the reactor is started up to produce the reaction product for a certain period of time, then shut down, and restarted later. However, in the production method according to PTL 1, the temperature of the heating medium after the shutdown is set 2° C. or 3° C. higher than the temperature of the heating medium before the shutdown (Example 1). Hence, PTL1 cannot solve the above-mentioned problem.

PTL 2 teaches a start-up method in obtaining (meth)acrylic acid by a gas-phase contact oxidation reaction, with use of a multitubular heat-exchanger type reactor which includes a plurality of reaction tubes each filled with a catalyst and a space formed between the reaction tubes. A (meth)acrolein-containing source gas is supplied into the reaction tubes while a heating medium is introduced into the space. With the proviso that. Th represents the temperature of the heating medium introduced into the space during the transition from the start of the source gas supply to the steady operation, and that Ts represents the temperature of the heating medium introduced into the space during the steady operation, Th and Ts satisfy −5<(Th−Ts)<2. However, PTL 2 does not disclose how to set the temperature of the heating medium in the restart period relative to the temperature of the heating medium in the initial start-up period. Hence, PTL 2 cannot solve the above-mentioned problem.

CITATION LIST

Patent Literature

[PTL 1] JP 2009-263352 A
[PTL 2] JP 2011-183313 A

SUMMARY OF INVENTION

Technical Problem

In view of the above-mentioned problem in the conventional art, the present invention has an object to provide a method for producing at least one oxidation product selected from the group consisting of acrolein and acrylic acid, which can alleviate concerns about deterioration of a gas-phase oxidation catalyst and reaction runaway in the restart period after the shutdown and which can allow the reaction to proceed in a stable state.

Solution to Problem

As a method for producing an oxidation catalyst, the present invention provides a method for producing at least one oxidation product selected from the group consisting of acrolein and acrylic acid, with use of a fixed-bed reactor filled with a gas-phase oxidation catalyst, by subjecting at least one source gas selected from the group consisting of propylene and acrolein to a gas-phase contact oxidation reaction while causing a heating medium to contact with or circulate through the fixed-bed reactor and thereby heating the fixed-bed reactor. A feature of this method resides in that a temperature of the heating medium when a load is maximum in a restart period after a shutdown is controlled to be lower than a temperature of the heating medium when a load is maximum in an initial start-up period.

The load in the initial start-up period is calculated by the following formula.

$$\text{Load in the initial start-up period} = \frac{\text{(gas flow rate of propylene and/or acrolein)}}{\left(\begin{array}{c}\text{target gas flow rate of}\\ \text{propylene and/or acrolein}\end{array}\right)}$$

The load in the restart period is calculated by the following formula. Preferably, the maximum load is 95 to 105%.

$$\text{Load in the restart period} = \frac{\text{(gas flow rate of propylene and/or acrolein)}}{\left(\begin{array}{c}\text{target gas flow rate of propylene and/or acrolein}\\ \text{in the initial start-up period}\end{array}\right)}$$

According to this method, the temperature of the heating medium when the load is maximum in the restart period after the shutdown is controlled to be lower than the temperature of the heating medium when the load is maximum in the initial start-up period. This arrangement can prevent a rise of the maximum temperature of the catalyst layer. Eventually, it is possible to alleviate concerns about deterioration of a gas-phase oxidation catalyst and reaction runaway and to allow the reaction to proceed in a stable state.

Advantageous Effects of Invention

The present invention can provide a method for producing at least one oxidation product selected from the group consisting of acrolein and acrylic acid, while alleviating concerns about deterioration of a gas-phase oxidation catalyst and reaction runaway in the restart period after the shutdown and allowing the reaction to proceed in a stable state.

DESCRIPTION OF EMBODIMENTS

Hereinafter, the present invention is described in detail.

A method for producing an oxidation product according to the present invention is a method for producing at least one oxidation product selected from the group consisting of acrolein and acrylic acid, with use of a fixed-bed reactor filled with a gas-phase oxidation catalyst (hereinafter simply called "catalyst"), by subjecting at least one source gas selected from the group consisting of propylene and acrolein to a gas-phase contact oxidation reaction while causing a heating medium to contact with or circulate through the fixed-bed reactor (hereinafter simply called "reactor") and thereby heating the fixed-bed reactor. In this method, the temperature of the heating medium when the load is maximum in the restart period after the shutdown is controlled to be lower than the temperature of the heating medium when the load is maximum in the initial start-up period.

In a particularly preferable embodiment, production of the oxidation product is restarted after the shutdown in a manner described herein within 9000 hours from the initial start-up of the reaction. The period of 9000 hours or less from the initial start-up of the reaction ensures a high catalyst activity and a great effect of preventing a runaway reaction or the like.

The reactor is not particularly limited, and may be a standard reactor for production of acrylic acid or the like. A gas-phase contact oxidation reaction using such a reactor may be performed by whichever of a so-called single-pass process or a so-called off-gas recycling process. The single-pass process is performed by introducing a mixed gas containing a source gas, oxygen and an inert gas (nitrogen, carbon dioxide, etc.) into the reactor, subjecting the source gas to a gas-phase contact oxidation reaction to generate an oxidation product, recovering the generated oxidation product, detoxifying the other substance, namely, by-product gas containing an inert gas as a major component and also containing oxygen, unreacted source gas, etc. (hereinafter abbreviated as off-gas) in a predetermined manner, and discharging the detoxified substance out of the system. The off-gas recycling process recycles a part or all of the off-gas as a mixed gas to be introduced into the reactor. The reactor structure is not particularly limited and may be, for example, a single-stage reactor, a tandem multistage reactor in which a first-stage reactor and a second-stage reactor are independent from each other and connected by tubing, or an integrated multistage reactor in which a first-stage reactor and a second-stage reactor are integrated.

In the production method according to the present invention, the reactor filled with a catalyst is not particularly limited, as exemplified below. A multitubular reactor is equipped with a plurality of reaction tubes in each of which a catalyst is filled as a catalyst layer, and is configured to circulate a heating medium between the reaction tubes. A plate reactor is equipped with a pair of heat transfer plates between which a catalyst is filled as a catalyst layer, and is configured to circulate a heating medium along the outer side of the heat transfer plates.

In the gas-phase contact oxidation reaction using such a reactor, a mixed gas containing a source gas and oxygen is introduced into the reactor and caused to circulate therein. The composition of the mixed gas is not particularly limited, and may be that of a mixed gas employed in a standard gas-phase contact oxidation reaction.

For generation of acrolein by a gas-phase contact oxidation reaction of a propylene-containing source gas, the composition of a mixed gas may be propylene 1 to 12 vol %, preferably 4 to 10 vol %; molecular oxygen 3 to 20 vol %, preferably 4 to 18 vol %; water vapor 0 to 60 vol %, preferably 1.6 to 50 vol %; and an inert gas (nitrogen, carbon dioxide, etc.) 20 to 80 vol %, preferably 30 to 60 vol %.

For generation of acrylic acid by a gas-phase contact oxidation reaction of an acrolein-containing source gas, the composition of a mixed gas may be acrolein 1 to 12 vol %, preferably 4 to 10 vol %; molecular oxygen 3 to 20 vol %, preferably 4 to 18 vol %; water vapor 0 to 60 vol %, preferably 1.6 to 50 vol %; and an inert gas (nitrogen, carbon dioxide, etc.) 20 to 80 vol %, preferably 30 to 60 vol %.

In the production method according to the present invention, the reactor is a multistage reactor which is equipped with a first-stage reactor filled with a first catalyst and a second-stage reactor filled with a second catalyst, the second-stage reactor being connected to a gas outlet side of the first-stage reactor. In the first-stage reactor, acrolein is produced by a gas-phase contact oxidation reaction of the propylene-containing source gas. In the second-stage reactor, acrylic acid is produced by a gas-phase contact oxidation reaction of the acrolein-containing source gas. In this case, outlet gas from the first-stage reactor may be supplied to the second-stage reactor, where necessary, with addition of molecular oxygen and an inert gas, etc.

The reaction temperature in the gas-phase contact oxidation reaction may be from 250° C. to 450° C., particularly from 250 to 350° C. The reaction pressure in the gas-phase contact oxidation reaction may be from 20 to 100 kPa, particularly from 25 to 80 kPa. The space velocity of the mixed gas and the source gas (gas flow rate/apparent volume of the filled catalyst) may be from 300 to 5000 hr$^{-1}$.

In the gas-phase contact oxidation reaction for generating acrolein from the propylene-containing source gas, a common catalyst for this gas-phase contact oxidation reaction may be employed without particular limitation. The catalyst may be a composite metal oxide which contains molybdenum, bismuth, nickel, etc. as essential ingredients, an example of which is a catalyst having a composition represented by Formula (1) below. Use of a catalyst represented by Formula (1) below enables generation of acrolein and acrylic acid from the propylene-containing source gas.

$$Mo_{12}Bi_aNi_bCo_cFe_dX_eY_fZ_gO_h \qquad (1)$$

[In Formula (1) above, Mo, Bi, Ni, Co, Fe and O represent molybdenum, bismuth, nickel, cobalt, iron and oxygen, respectively. X represents at least one element selected from the group consisting of magnesium, calcium, manganese, copper, zinc, tin, cerium and samarium. Y represents at least one element selected from the group consisting of boron, phosphorus, arsenic, antimony, tungsten, chromium and titanium. Z represents at least one element selected from the group consisting of sodium, potassium, rubidium, thallium and cesium. Lower-case letters a, b, c, d, e, f, g and h represent atomic ratios of the respective elements relative to 12 molybdenum atoms, wherein $0.1 \leq a \leq 7$, $0.5 \leq b+c \leq 20$, $0.5 \leq d \leq 8$, $0 \leq e \leq 10$, $0 \leq f \leq 10$ and $0 \leq g \leq 0.2$ and wherein h is a number determined by oxidation states of the elements except oxygen.]

In the gas-phase contact oxidation reaction for generating acrylic acid from the acrolein-containing source gas, a common catalyst for this gas-phase contact oxidation reaction may be employed without particular limitation. The catalyst may be a composite metal oxide which contains molybdenum, vanadium, copper, antimony, etc. as essential ingredients, an example of which is a catalyst having a composition represented by Formula (2) below.

$$Mo_{12}V_hW_iCu_jSb_kX_lY_mZ_nO_o \quad (2)$$

[In Formula (2) above, Mo, V, W, Cu, Sb and O represent molybdenum, vanadium, tungsten, copper, antimony and oxygen, respectively. X represents at least one element selected from the group consisting of alkali metals and thallium. Y represents at least one element selected from the group consisting of magnesium, calcium, strontium, barium and zinc. Z represents at least one element selected from the group consisting of niobium, cerium, tin, chromium, manganese, iron, cobalt, samarium, germanium, titanium and arsenic. Lowercase letters h, i, j, l, m, n and o represent atomic ratio of the respective elements relative to 12 molybdenum atoms, wherein $0<h \leq 10$, $0 \leq i \leq 10$, $0<j \leq 6$, $0<k \leq 10$, $0 \leq l \leq 0.5$, $0 \leq m \leq 1$ and $0 \leq n \leq 6$ and wherein o is a number determined by oxidation states of the elements except oxygen.]

The catalyst is formed in a predetermined shape to be easily filled into the reactor, particularly into the reaction tubes of the multitubular reactor. The shape of the catalyst is not particularly limited and may be, for example, spherical, flat with a circular cross section, columnar, cylindrical, prismatic or the like. The method for shaping the catalyst may be, for example, tableting, extrusion molding, and shaping by a granulator.

On the upstream of the catalyst layer, an inert filler having no catalytic activity may be filled to form an inert filler layer. In this context, "upstream" means an inlet side of the reactor from which the source gas is introduced. Usually, the inert filler layer is formed at an upper part of the reactor (if the source gas is introduced to flow in a down-flow direction) or at a lower part of the reactor (if the source gas is introduced to flow in an up-flow direction).

The inert filler simply needs to be a substance which has substantially no reaction activity against the source gas during the gas-phase contact oxidation reaction, and is not particularly limited. As the inert filler, use may be made of oxides and complex oxides of various metal elements. Oxides include alumina (which may be alundum serving as an abrasive, such as α-alumina), silica, zirconia, silicon carbide (which may be carborundum serving as an abrasive) and the like. Complex oxides include silicon/aluminium complex oxide (mullite), silicon/titanium complex oxide, silicon/zirconium complex oxide, aluminium/titanium complex oxide, aluminium/zirconium complex oxide and the like. The inert filler may also be metals such as stainless steel and aluminium. Preferable inert fillers are oxides of alumina, silica and zirconia, etc. and complex oxides such as mullite. A particularly preferable inert filler is mainly composed of alumina and/or silica. The inert filler may be used alone or in combination with two or more species. In the above description, the phrase "mainly composed of" means that the total content of alumina and silica is 85 mass % or more when the entire amount of the inert filler is 100 mass %.

The shape of the inert filler is not particularly limited, and may be spherical, annular, linear, strip-shaped or in other shapes. Considering the work efficiency for extracting the inert filler for replacement or the like, a spherical shape is preferable. The maximum size of the inert filler, which depends on the inner diameter of the reaction tubes employed in the gas-phase contact oxidation reaction, is preferably from 2 to 10 mm.

The heating medium simply needs to be capable of maintaining the inside of the reactor at a predetermined reaction temperature, and is not particularly limited. Suitable heating mediums include molten salts, particularly niter (a molten mixture of potassium nitrate, sodium nitrate and sodium nitrite) for their broad usable temperature range, great heat capacity, and relatively low viscosity.

The temperature of the heating medium can be set within the range of the above-mentioned reaction temperature, namely from 250 to 450° C., particularly from 250 to 350° C.

In a desirable embodiment, the temperature of the heating medium when the load is maximum in the restart period after the shutdown is controlled to be lower than the temperature of the heating medium when the load is maximum in the initial start-up period by 1° C. to 30° C., preferably 2° C. to 20° C., more preferably 3° C. to 15° C., and further preferably 4° C. to 10° C.

EXAMPLES

Hereinafter, the present invention is described more specifically by way of Examples.

In following Examples, the unit "part(s)" means mass part(s) and the unit "%" means mass %, unless otherwise specified. The propylene conversion and the total yield of acrylic acid and acrolein are defined by Formulas (5) and (6) below.

$$\text{Propylene conversion (mol \%)} = \frac{\text{(molar amount of reacted propylene)}}{\text{(molar amount of supplied propylene)}} \times 100 \quad (5)$$

$$\text{Total yield of acrylic acid and acrolein (mol \%)} = \frac{\begin{pmatrix}\text{total molar amount of generated}\\ \text{acrylic acid and acrolein}\end{pmatrix}}{\text{(molar amount of supplied propylene)}} \times 100 \quad (6)$$

(1) Preparation of Propylene Oxidation Catalysts 1 and 2

Aqueous solutions (A), (B) and (C) were prepared separately in the following manner. For Aqueous solution (A), 800.0 g of ammonium molybdate and 3.7 g of potassium nitrate were dissolved in 3000 ml of distilled water with heating and stirring. For Aqueous solution (B), 571.5 g of cobalt nitrate, 162.9 g of nickel nitrate and 274.6 g of ferric nitrate were dissolved in 1000 ml of distilled water. For Aqueous solution (C), 164.9 g of bismuth nitrate was dissolved in 200 ml of distilled water which was made acidic by addition of 79.3 g of concentrated nitric acid. Thereafter, Aqueous solutions (B) and (C) were, in this order, added dropwise and mixed into Aqueous solution (A) with vigorous stirring.

The generated suspension liquid was dried by use of a spray drier and subjected to preliminary calcination at 440° C. for three hours to prepare preliminary calcined powder. Next, 300 g of this preliminary calcined powder was mixed with crystalline cellulose as a forming auxiliary to give a mixture. Into a tumbling granulator, 300 g of alumina support having a mean particle diameter of 4.0 mm was fed first, and next, the above mixture and an aqueous solution of 30% glycerol as a binder were added simultaneously. Thus obtained were active component-supported particles in which the mixture was supported on the support at a loading of 50%. Thereafter, the active component-supported particles were dried at room temperature for 15 hours, calcined under airflow at 550° C. for five hours to give Propylene Oxidation Catalyst 1. Propylene Oxidation Catalyst 2 was prepared in the same manner as Propylene Oxidation Catalyst 1, except that the calcination conditions were changed to 520° C. for five hours. In thus obtained Propylene Oxidation Catalysts 1 and 2, the mean particle diameter was 4.7 mm, and the composition of the catalytically active component except oxygen was Mo;12, Bi;1.7, Ni;2.8, Fe;1.8, Co;5.2, K;0.1 in the atomic ratio.

(2) Preparation of Propylene Oxidation Catalyst 3

Aqueous solutions (A), (B) and (C) were prepared separately in the following manner. For Aqueous solution (A), 800.0 g of ammonium molybdate and 1.8 g of potassium nitrate were dissolved in 3000 ml of distilled water with heating and stirring. For Aqueous solution (B), 714.4 g of cobalt nitrate, 329.4 g of nickel nitrate and 305.1 g of ferric nitrate were dissolved in 1000 ml of distilled water. For Aqueous solution (C), 183.2 g of bismuth nitrate was dissolved in 190 ml of distilled water which was made acidic by addition of 46.6 g of concentrated nitric acid. Thereafter, Aqueous solutions (B) and (C) were, in this order, added dropwise and mixed into Aqueous solution (A) with vigorous stirring.

The generated suspension liquid was dried by use of a spray drier and subjected to preliminary calcination at 440° C. for three hours to prepare preliminary calcined powder. Next, 300 g of this preliminary calcined powder was mixed with crystalline cellulose as a forming auxiliary to give a mixture. Into a tumbling granulator, 300 g of alumina support having a mean particle diameter of 5.2 mm was fed first, and next, the above-mentioned mixture and an aqueous solution of 30% glycerol as a binder were added simultaneously. Thus obtained were active component-supported particles in which the mixture was supported on the support at a loading of 50%. Thereafter, the active component-supported particles were dried at room temperature for 15 hours, calcined under airflow at 540° C. for five hours to give Propylene Oxidation Catalyst 3. In thus obtained Propylene Oxidation Catalyst 3, the mean particle diameter was 5.3 mm, and the composition of the catalytically active component except oxygen was Mo;12, Bi;1.0, Ni;3.0, Fe;2.0, Co;6.5, K;0.05 in the atomic ratio.

(3) Preparation of Propylene Oxidation Catalyst 4

Propylene Oxidation Catalyst 4 was prepared in the same manner as Propylene Oxidation Catalyst 3, except that potassium nitrate was replaced by cesium nitrate and that the calcination temperature was changed to 530° C. In thus obtained Propylene Oxidation Catalyst 4, the mean particle diameter was 5.3 mm, and the composition of the catalytically active component except oxygen was Mo;12, Bi;1.0, Ni;3.0, Fe;2.0, Co;6.5, Cs;0.05 in the atomic ratio.

Example 1

In this Example, acrolein and acrylic acid were produced by a gas-phase contact oxidation reaction of propylene, with use of a production apparatus provided with a multistage reactor. The multistage reactor was composed of a first-stage reactor which was equipped with first reaction tubes each filled with a first catalyst, and a second-stage reactor which was equipped with second reaction tubes and which was connected to a gas outlet side of the first-stage reactor. The production apparatus was further composed of first and second heating medium circulation systems for circulating niter (a molten mixture of potassium nitrate, sodium nitrate and sodium nitrite), as a heating medium, by respective pumps such that the niter can contact the outer side of the first and second reaction tubes, first and second heaters for heating the niter to be brought into contact with the outer side of the first and second reaction tubes, and a thermocouple thermometer for measuring the temperature of the first and second catalyst layers formed respectively in the first and second reaction tubes.

The first-stage reactor for propylene oxidation was provided with an aftercooler at an outlet region thereof. In the first reaction tubes (inner diameter 25 mm) of this first-stage reactor, Propylene Oxidation Catalyst 1 mentioned above was filled as the first catalyst up to 140 cm to form a first oxidation catalyst layer (on the source gas inlet side), and Propylene Oxidation Catalyst 2 was filled up to 300 cm on the gas outlet side to form a second oxidation catalyst layer (on the gas outlet side). Thus formed was a catalyst layer with a total height of 440 cm.

After the catalyst was filled in the above manner, the first-stage reactor was connected to the second-stage reactor. A mixed gas composed of propylene, air and water vapor in which the molar ratio (the volume ratio) of propylene/oxygen/nitrogen/water vapor was 1/1.75/6.59/3.54 was introduced into the first-stage reactor under the condition that the space velocity of propylene relative to the amount of catalyst filled in the first-stage reactor was 105 $h^{-1}$. In the first-stage reactor, propylene was subjected to a gas-phase contact oxidation reaction to give acrolein and acrylic acid.

(Initial Start-Up)

In the initial start-up period, the temperature of the heating medium (the reaction temperature) in the first-stage reactor was 335° C., and the 100% load in the initial start-up period was achieved at 335° C. At this moment, the maximum temperature (the hot spot temperature) of the catalyst layer in the first-stage reactor was 370° C. Immediately after the initial start-up, when the cumulative reaction time from the initial start-up of the reaction reached 135 hours, the reaction performance was checked at the heating medium temperature of 330° C. It turned out that the propylene conversion was 98.2%, and that the total yield of acrolein and acrylic acid was 89.5%. At this moment, the maximum temperature (the hot spot temperature) of the catalyst layer in the first-stage reactor was 372° C.

(Stable Operation Before Shutdown)

The reaction was stabilized when the cumulative reaction time from the initial start-up of the reaction reached 300 hours. Hence, by setting the temperature of the heating medium in the first-stage reactor at 326° C., the production apparatus was allowed to run on a stable operation mode. After the stable operation continued under this temperature condition, the reaction performance was checked when the cumulative reaction time from the initial start-up reached 2195 hours. It turned out that the propylene conversion was 98.3%, and that the total yield of acrolein and acrylic acid was 89.7%. At this moment, the maximum temperature of the catalyst layer in the first-stage reactor was 381° C.

(Shutdown)

When the cumulative reaction time from the initial start-up of the reaction reached about 2200 hours, the production apparatus was suddenly shut down due to a power failure caused by a natural disaster. After the shutdown, the temperature of the heating medium fell gradually during the power failure by natural cooling. Also after the shutdown, the reaction stopped because propylene and the air-containing mixed gas were replaced by nitrogen gas.

(Restart after Shutdown)

After power recovery, the production apparatus was restarted five hours after the shutdown. When the load reached 100% in this restart period (when the cumulative reaction time from the initial start-up of the reaction reached 2205 hours), the temperature of the heating medium in the first-stage reactor was set at 331° C., which was 4° C. lower than the temperature when the 100% load was achieved in the initial start-up period and 5° C. higher than the temperature at the moment of shutdown. In this restart period, the maximum temperature of the catalyst layer in the first-stage reactor was 383° C.

After the 100% load was achieved in the restart period and when the cumulative reaction time from the initial start-up of the reaction reached 2224 hours, the reaction performance was checked at the heating medium temperature of 326° C. It turned out that the propylene conversion was 98.3%, and that the total yield of acrolein and acrylic acid was 89.9%. At this moment, the maximum temperature of the catalyst layer in the first-stage reactor was 384° C., which was low enough to prevent reaction runaway in the restart period. The yield in the restart period was as good as the yield before the shutdown.

(Stable Operation after Restart)

The reaction had been stabilized when the cumulative reaction time from the initial start-up of the reaction reached 2901 hours. Hence, the reaction performance was checked at the heating medium temperature in the first-stage reactor of 326° C. It turned out that the propylene conversion was 98.4%, and that the total yield of acrolein and acrylic acid was 89.7%. At this moment, the maximum temperature of the catalyst layer in the first-stage reactor was 377° C. The reaction performance was further checked when the cumulative reaction time from the initial start-up of the reaction reached 8979 hours, in a state where the reaction was stabilized at the heating medium temperature of 327° C. It turned out that the propylene conversion was 98.4%, and that the total yield of acrolein and acrylic acid was 89.9%. At this moment, the maximum temperature of the catalyst layer in the first-stage reactor was 366° C.

(Shutdown)

When the cumulative reaction time from the initial start-up of the reaction reached about 9000 hours, the production apparatus was shut down for a scheduled repair.

(Restart after Shutdown)

After the finish of the scheduled repair, the production apparatus was restarted 100 hours after the shutdown. When the load reached 100% in this restart period (when the cumulative reaction time from the initial start-up of the reaction reached 9004 hours), the temperature of the heating medium in the first-stage reactor was set at 331° C., which was 4° C. lower than the temperature when the 100% load was achieved in the initial start-up period and 4° C. higher than the temperature at the moment of shutdown. In this restart period, the maximum temperature of the catalyst layer in the first-stage reactor was a safe temperature of 368° C.

After the 100% load was achieved in the restart period and when the cumulative reaction time from the initial start-up of the reaction reached 9057 hours, the reaction performance was checked at the heating medium temperature of 325° C. It turned out that the propylene conversion was 98.5%, and that the total yield of acrolein and acrylic acid was 89.5%. At this moment, the maximum temperature of the catalyst layer in the first-stage reactor was 367° C., which was low enough to prevent reaction runaway in the restart period.

(Stable Operation after Restart)

When the cumulative reaction time from the initial start-up of the reaction reached 9585 hours, the reaction performance was checked at the heating medium temperature of 327° C. It turned out that the propylene conversion was 98.5%, and that the total yield of acrolein and acrylic acid was 89.6%. Thus, the reaction performance recovered substantially to the level before the shutdown. At this moment, the maximum temperature of the catalyst layer in the first-stage reactor was 367° C. In the stable operation after the shutdown, the conversion and the yield were as good as the values in the stable operation before the shutdown, and the maximum temperature of the catalyst layer was also similar to the maximum temperature in the stable operation before the shutdown. These results proved the capability of stable operation. For each period, Table 1 shows the temperature of the heating medium and the maximum temperature of the catalyst layer in the first-stage reactor, along with the reaction performance.

TABLE 1

| | Cumulative reaction time from initial start of reaction (hr) | First-stage reactor for propylene oxidation | | Yield of | |
|---|---|---|---|---|---|
| | | Temperature of heating medium (° C.) | Max. temperature of catalyst layer (° C.) | Propylene conversion (%) | acrolein + acrylic acid (%) |
| Initial start-up | 5 | 335 | 370 | — | — |
| Immediately after initial start-up | 135 | 330 | 372 | 98.2 | 89.5 |
| Stable operation before shutdown | 2195 | 326 | 381 | 98.3 | 89.7 |
| Restart after shutdown | 2205 | 331 | 383 | — | — |
| Immediately after restart after shutdown | 2224 | 326 | 384 | 98.3 | 89.9 |
| Stable operation after restart | 2901 | 326 | 377 | 98.4 | 89.7 |

TABLE 1-continued

|  | Cumulative reaction time from initial start of reaction (hr) | First-stage reactor for propylene oxidation | | | Yield of |
|---|---|---|---|---|---|
|  |  | Temperature of heating medium (° C.) | Max. temperature of catalyst layer (° C.) | Propylene conversion (%) | acrolein + acrylic acid (%) |
| Stable operation before shutdown | 8979 | 327 | 366 | 98.4 | 89.9 |
| Restart after shutdown | 9004 | 331 | 368 | — | — |
| Immediately after restart after shutdown | 9057 | 325 | 367 | 98.5 | 89.5 |
| Stable operation after restart | 9585 | 327 | 367 | 98.5 | 89.6 |

Example 2

The production apparatus employed in this example was similar to the one employed in Example 1. The first-stage reactor for propylene oxidation was provided with an aftercooler at an outlet region thereof. In the first reaction tubes (inner diameter 25 mm) of this first-stage reactor, a mixture of Propylene Oxidation Catalyst 4 and silica alumina having a diameter of 5.2 mm, mixed in a weight ratio of 85:15, was filled as the first catalyst up to 80 cm to form a first oxidation catalyst layer (on the source gas inlet side). Next, Propylene Oxidation Catalyst 4 was filled up to 80 cm to form a second oxidation catalyst layer (closer to the gas outlet side than the first oxidation catalyst layer). Further, Propylene Oxidation Catalyst 3 was filled up to 190 cm to form a third oxidation catalyst layer (on the gas outlet side). Thus formed was a catalyst layer with a total height of 350 cm.

After the catalyst was filled in the above manner, the first-stage reactor was connected to the second-stage reactor. A mixed gas composed of propylene, air, water vapor and nitrogen in which the molar ratio (the volume ratio) of propylene/oxygen/nitrogen/water vapor was 1/1.7/8.8/1 was introduced into the first-stage reactor under the condition that the space velocity of propylene relative to the amount of catalyst filled in the first-stage reactor was 100 h$^{-1}$. In the first-stage reactor, propylene was subjected to a gas-phase contact oxidation reaction. In this example, propylene was subjected to a gas-phase contact oxidation reaction in the first-stage reactor to give acrolein and acrylic acid, and acrolein was subjected to a gas-phase contact oxidation reaction in the second-stage reactor to give acrylic acid.

(Initial Start-Up)

In the initial start-up period, the temperature of the heating medium (the reaction temperature) in the first-stage reactor was 331° C., and the 100% load in the initial start-up period was achieved at 331° C. At this moment, the maximum temperature (the hot spot temperature) of the catalyst layer in the first-stage reactor was 394° C. Immediately after the initial start-up, when the cumulative reaction time from the initial start-up of the reaction reached 23 hours, the reaction performance was checked at the heating medium temperature of 331° C. It turned out that the propylene conversion was 98.8%, and that the total yield of acrolein and acrylic acid was 91.8%. At this moment, the maximum temperature (the hot spot temperature) of the catalyst layer in the first-stage reactor was 378° C.

(Stable Operation Before Shutdown)

When the cumulative reaction time from the initial start-up of the reaction reached 600 hours, the production apparatus was allowed to run on a stable operation mode by setting the temperature of the heating medium in the first-stage reactor at 322° C. After the stable operation continued under this temperature condition, the reaction performance was checked when the cumulative reaction time from the initial start-up reached 2492 hours. It turned out that the propylene conversion was 98.6%, and that the total yield of acrolein and acrylic acid was 91.6%. At this moment, the maximum temperature of the catalyst layer in the first-stage reactor was 387° C.

(Shutdown)

When the cumulative reaction time from the initial start-up of the reaction reached about 2500 hours, the production apparatus was shut down for a scheduled repair. After the shutdown, the reaction stopped because propylene and the air-containing mixed gas were replaced by nitrogen gas.

(Restart after Shutdown)

Later, after the finish of the scheduled repair, the production apparatus was restarted 100 hours after the shutdown. When the load reached 100% in this restart period (when the cumulative reaction time from the initial start-up of the reaction reached 2617 hours), the temperature of the heating medium in the first-stage reactor was set at 322° C., which was 9° C. lower than the temperature when the 100% load was achieved in the initial start-up period and equal to the temperature at the moment of shutdown. In this restart period, the maximum temperature of the catalyst layer in the first-stage reactor was 376° C.

After the 100% load was achieved in the restart period and when the cumulative reaction time from the initial start-up of the reaction reached 2641 hours, the reaction performance was checked at the heating medium temperature of 322° C. It turned out that the propylene conversion was 98.2%, and that the total yield of acrolein and acrylic acid was 92.3%. At this moment, the maximum temperature of the catalyst layer in the first-stage reactor was 385° C., which was low enough to prevent reaction runaway in the restart period. The yield in the restart period was also favorable.

(Stable Operation after Restart)

The reaction was stabilized when the cumulative reaction time from the initial start-up of the reaction reached 2973 hours. Hence, the reaction performance was checked at the heating medium temperature in the first-stage reactor of 322° C. It turned out that the propylene conversion was 98.7%, and that the total yield of acrolein and acrylic acid was 91.6%. At this moment, the maximum temperature of the catalyst layer in the first-stage reactor was 388° C.

The reaction performance was further checked when the cumulative reaction time from the initial start-up of the reaction reached 9554 hours, in a state where the reaction was stabilized at the heating medium temperature of 323° C. It turned out that the propylene conversion was 98.6%, and that the total yield of acrolein and acrylic acid was 91.2%. At this moment, the maximum temperature of the catalyst layer in the first-stage reactor was 377° C.

(Shutdown)

When the cumulative reaction time from the initial start-up of the reaction reached about 9560 hours, the production apparatus was shut down for a scheduled repair.

(Restart after Shutdown)

After the finish of the scheduled repair, the production apparatus was restarted 100 hours after the shutdown. When the load reached 100% in this restart period (when the cumulative reaction time from the initial start-up of the reaction reached 9562 hours), the temperature of the heating medium in the first-stage reactor was set at 323° C., which was 8° C. lower than the temperature when the 100% load was achieved in the initial start-up period and equal to the temperature at the moment of shutdown. In this restart period, the maximum temperature of the catalyst layer in the first-stage reactor was a safe temperature of 383° C.

After the 100% load was achieved in the restart period and when the cumulative reaction time from the initial start-up of the reaction reached 9581 hours, the reaction performance was checked at the heating medium temperature of 323° C. It turned out that the propylene conversion was 98.7%, and that the total yield of acrolein and acrylic acid was 91.7%. At this moment, the maximum temperature of the catalyst layer in the first-stage reactor was 378° C., which was low enough to prevent reaction runaway in the restart period.

(Stable Operation after Restart)

When the cumulative reaction time from the initial start-up of the reaction reached 9917 hours, the reaction performance was checked at the heating medium temperature of 322° C. It turned out that the propylene conversion was 98.6%, and that the total yield of acrolein and acrylic acid was 91.6%. Thus, the reaction performance was substantially equivalent to the level before the shutdown. At this moment, the maximum temperature of the catalyst layer in the first-stage reactor was 376° C. In the stable operation after the shutdown, the conversion and the yield were as good as the values in the stable operation before the shutdown, and the maximum temperature of the catalyst layer was also similar to the maximum temperature in the stable operation before the shutdown. These results proved the capability of stable operation. For each period, Table 2 shows the temperature of the heating medium and the maximum temperature of the catalyst layer in the first-stage reactor, along with the reaction performance.

TABLE 2

|  | Cumulative reaction time from initial start of reaction (hr) | First-stage reactor for propylene oxidation | | Yield of | |
| --- | --- | --- | --- | --- | --- |
|  |  | Temperature of heating medium (° C.) | Max. temperature of catalyst layer (° C.) | Propylene conversion (%) | acrolein + acrylic acid (%) |
| Initial start-up | 4 | 331 | 394 | — | — |
| Immediately after initial start-up | 23 | 331 | 378 | 98.8 | 91.8 |
| Stable operation before shutdown | 2492 | 322 | 387 | 98.6 | 91.6 |
| Restart after shutdown | 2617 | 322 | 376 | — | — |
| Immediately after restart after shutdown | 2641 | 322 | 385 | 98.2 | 92.3 |
| Stable operation after restart | 2973 | 322 | 388 | 98.7 | 91.6 |
| Stable operation before shutdown | 9554 | 323 | 377 | 98.6 | 91.2 |
| Restart after shutdown | 9562 | 323 | 383 | — | — |
| Immediately after restart after shutdown | 9581 | 323 | 378 | 98.7 | 91.7 |
| Stable operation after restart | 9917 | 322 | 376 | 98.6 | 91.6 |

INDUSTRIAL APPLICABILITY

The present invention is applicable to production of at least one oxidation product selected from the group consisting of acrolein and acrylic acid, with use of a fixed-bed reactor filled with a gas-phase oxidation catalyst, by subjecting at least one source gas selected from the group consisting of propylene and acrolein to a gas-phase contact oxidation reaction.

The present invention can be embodied and practiced in other different forms without departing from the spirit and essential characteristics of the present invention. Therefore, the above-described embodiments are considered in all respects as illustrative and not restrictive. The scope of the invention is indicated by the appended claims rather than by the foregoing description. All variations and modifications falling within the equivalency range of the appended claims are intended to be embraced therein.

The present application claims priority of Japanese Patent Application No. 2016-66023 filed Mar. 29, 2016. The contents of all printed publications, patents and patent applications (including the above-mentioned Japanese patent application) cited herein are incorporated herein by reference in their entirety.

The invention claimed is:

1. A method for producing at least one oxidation product selected from the group consisting of acrolein and acrylic acid, with use of a fixed-bed reactor filled with a gas-phase oxidation catalyst, by subjecting at least one source gas selected from the group consisting of propylene and acrolein to a gas-phase contact oxidation reaction while causing a heating medium to contact with or circulate through the fixed-bed reactor and thereby heating the fixed-bed reactor,
wherein the temperature of the heating medium at maximum load in the restart period after a shutdown is controlled to be lower than the temperature of the heating medium at maximum load in the initial start-up period.

2. The method for producing an oxidation product according to claim 1, wherein production of the oxidation product is restarted after the shutdown within 9000 hours after an initial start-up of the reaction.

3. The method for producing an oxidation product according to claim 1,
wherein, in the restart period after the shutdown, propylene as the source gas is subjected to the gas-phase contact oxidation reaction to produce acrolein and acrylic acid, with use of the fixed-bed reactor filled with a gas-phase oxidation catalyst which has a composition represented by following Formula (1), $$Mo_{12}Bi_aNi_bCo_cFe_dX_eY_fZ_gO_h \qquad (1)$$

wherein Mo, Bi, Ni, Co, Fe and O represent molybdenum, bismuth, nickel, cobalt, iron and oxygen, respectively; X represents at least one element selected from the group consisting of magnesium, calcium, manganese, copper, zinc, tin, cerium and samarium; Y represents at least one element selected from the group consisting of boron, phosphorus, arsenic, antimony, tungsten, chromium and titanium; Z represents at least one element selected from the group consisting of sodium, potassium, rubidium, thallium and cesium; a, b, c, d, e, f, g and h represent atomic ratios of the respective elements relative to 12 molybdenum atoms, wherein $0.1 \leq a \leq 7$, $0.5 \leq b+c \leq 20$, $0.5 \leq d \leq 8$, $0 \leq e \leq 10$, $0 \leq f \leq 10$ and $0 \leq g \leq 0.2$ and wherein h is a number determined by oxidation states of the elements except oxygen.

4. The method for producing an oxidation product according to claim 1,
wherein the fixed-bed reactor is a multistage fixed-bed reactor which is equipped with a first fixed-bed reactor filled with a first gas-phase oxidation catalyst and a second-stage fixed-bed reactor filled with a second gas-phase oxidation catalyst, the second-stage fixed-bed reactor being connected to a gas outlet side of the first-stage fixed-bed reactor, and
wherein acrolein is produced in the first-stage fixed-bed reactor by a gas-phase contact oxidation reaction of propylene, and acrylic acid is produced in the second-stage fixed-bed reactor by a gas-phase contact oxidation reaction of the thus produced acrolein.

5. The method for producing an oxidation product according to claim 2,
wherein, in the restart period after the shutdown, propylene as the source gas is subjected to the gas-phase contact oxidation reaction to produce acrolein and acrylic acid, with use of the fixed-bed reactor filled with a gas-phase oxidation catalyst which has a composition represented by following Formula (1), $$Mo_{12}Bi_aNi_bCo_cFe_dX_eY_fZ_gO_h \qquad (1)$$

wherein Mo, Bi, Ni, Co, Fe and O represent molybdenum, bismuth, nickel, cobalt, iron and oxygen, respectively; X represents at least one element selected from the group consisting of magnesium, calcium, manganese, copper, zinc, tin, cerium and samarium; Y represents at least one element selected from the group consisting of boron, phosphorus, arsenic, antimony, tungsten, chromium and titanium; Z represents at least one element selected from the group consisting of sodium, potassium, rubidium, thallium and cesium; a, b, c, d, e, f, g and h represent atomic ratios of the respective elements relative to 12 molybdenum atoms, wherein $0.1 \leq a \leq 7$, $0.5 \leq b+c \leq 20$, $0.5 \leq d \leq 8$, $0 \leq e \leq 10$, $0 \leq f \leq 10$ and $0 \leq g \leq 0.2$ and wherein h is a number determined by oxidation states of the elements except oxygen.

6. The method for producing an oxidation product according to claim 2,
wherein the fixed-bed reactor is a multistage fixed-bed reactor which is equipped with a first fixed-bed reactor filled with a first gas-phase oxidation catalyst and a second-stage fixed-bed reactor filled with a second gas-phase oxidation catalyst, the second-stage fixed-bed reactor being connected to a gas outlet side of the first-stage fixed-bed reactor, and
wherein acrolein is produced in the first-stage fixed-bed reactor by a gas-phase contact oxidation reaction of propylene, and acrylic acid is produced in the second-stage fixed-bed reactor by a gas-phase contact oxidation reaction of the thus produced acrolein.

7. The method for producing an oxidation product according to claim 3,
wherein the fixed-bed reactor is a multistage fixed-bed reactor which is equipped with a first fixed-bed reactor filled with a first gas-phase oxidation catalyst and a second-stage fixed-bed reactor filled with a second gas-phase oxidation catalyst, the second-stage fixed-bed reactor being connected to a gas outlet side of the first-stage fixed-bed reactor, and
wherein acrolein is produced in the first-stage fixed-bed reactor by a gas-phase contact oxidation reaction of propylene, and acrylic acid is produced in the second-stage fixed-bed reactor by a gas-phase contact oxidation reaction of the thus produced acrolein.

8. The method for producing an oxidation product according to claim 5,
wherein the fixed-bed reactor is a multistage fixed-bed reactor which is equipped with a first fixed-bed reactor filled with a first gas-phase oxidation catalyst and a second-stage fixed-bed reactor filled with a second gas-phase oxidation catalyst, the second-stage fixed-bed reactor being connected to a gas outlet side of the first-stage fixed-bed reactor, and
wherein acrolein is produced in the first-stage fixed-bed reactor by a gas-phase contact oxidation reaction of propylene, and acrylic acid is produced in the second-stage fixed-bed reactor by a gas-phase contact oxidation reaction of the thus produced acrolein.

* * * * *